(12) United States Patent
Takahashi et al.

(10) Patent No.: US 9,109,974 B2
(45) Date of Patent: Aug. 18, 2015

(54) TIRE SHAPE INSPECTION METHOD AND TIRE SHAPE INSPECTION APPARATUS

(71) Applicant: Kobe Steel, Ltd., Hyogo (JP)

(72) Inventors: Eiji Takahashi, Hyogo (JP); Toshiyuki Tsuji, Hyogo (JP); Masato Kannaka, Hyogo (JP)

(73) Assignee: Kobe Steel, Ltd., Hyogo (JP)

( * ) Notice: Subject to any disclaimer, the term of this patent is extended or adjusted under 35 U.S.C. 154(b) by 0 days.

(21) Appl. No.: 14/351,933

(22) PCT Filed: Oct. 2, 2012

(86) PCT No.: PCT/JP2012/075484
§ 371 (c)(1),
(2) Date: Apr. 15, 2014

(87) PCT Pub. No.: WO2013/069389
PCT Pub. Date: May 16, 2013

(65) Prior Publication Data
US 2014/0283591 A1 Sep. 25, 2014

(30) Foreign Application Priority Data
Nov. 7, 2011 (JP) ................................ 2011-243270

(51) Int. Cl.
*G01M 17/02* (2006.01)
*G01B 11/245* (2006.01)
(Continued)

(52) U.S. Cl.
CPC ............. *G01M 17/02* (2013.01); *G01B 11/245* (2013.01); *G01B 11/2522* (2013.01); *G01M 17/027* (2013.01); *B60C 13/003* (2013.01)

(58) Field of Classification Search
CPC ... G01M 17/02; G01M 17/027; G01B 11/245

USPC ............ 382/141, 143; 356/237.1, 237.2, 614, 356/625–640; 348/86
See application file for complete search history.

(56) References Cited

U.S. PATENT DOCUMENTS 4,910,411 A * 3/1990 Teraguchi et al. ....... 250/559.44
6,381,547 B1 * 4/2002 Heirtzler et al. ................ 702/39
(Continued)

FOREIGN PATENT DOCUMENTS

JP 2004-156919 A 6/2004
JP 2005-331274 A 12/2005
(Continued)

OTHER PUBLICATIONS

International Search Report; PCT/JP2012/075484; Dec. 4, 2012.
(Continued)

*Primary Examiner* — Samir Ahmed
(74) *Attorney, Agent, or Firm* — Studebaker & Brackett PC

(57) ABSTRACT

A tire shape inspection method executes the following steps: first, as a teaching operation step, boundary lines of the bulge and dent marks are detected in a sample source image of a sample tire, a mask image is generated which denotes the boundary lines, regions are removed from the sample source image which correspond to the boundary lines which are denoted in the mask image, and a height offset image is generated which represents the heights of the remaining regions with one or more offset values. Next, as an inspection operation step, the height offset image is subtracted from an inspection image of the inspection tire, the boundary regions which the mask image represents are removed, and, on the basis of the obtained bulge/dent removal image, shape defects of the sidewall surfaces of the inspection tire are inspected.

5 Claims, 9 Drawing Sheets

(51) Int. Cl.
  *G01B 11/25* (2006.01)
  *B60C 13/00* (2006.01)

(56) References Cited

U.S. PATENT DOCUMENTS

| | | | |
|---|---|---|---|
| 6,831,996 B1* | 12/2004 | Williams et al. | 382/141 |
| 7,738,120 B2* | 6/2010 | Braghiroli | 356/635 |
| 8,284,393 B2* | 10/2012 | Takahashi et al. | 356/237.1 |
| 2007/0209431 A1 | 9/2007 | Fujisawa et al. | |
| 2008/0218742 A1 | 9/2008 | Sakoda et al. | |
| 2011/0069323 A1* | 3/2011 | Takahashi et al. | 356/625 |
| 2012/0242824 A1 | 9/2012 | Takahashi et al. | |

FOREIGN PATENT DOCUMENTS

| | | |
|---|---|---|
| JP | 2008-221896 A | 9/2008 |
| JP | 2010-181320 A | 8/2010 |
| JP | 2011-141260 A | 7/2011 |
| TW | 201131152 A | 9/2011 |

OTHER PUBLICATIONS

Written Opinion of the International Searching Authority; PCT/JP2012/075484; Dec. 4, 2012.

* cited by examiner

FIG. 1
(a)
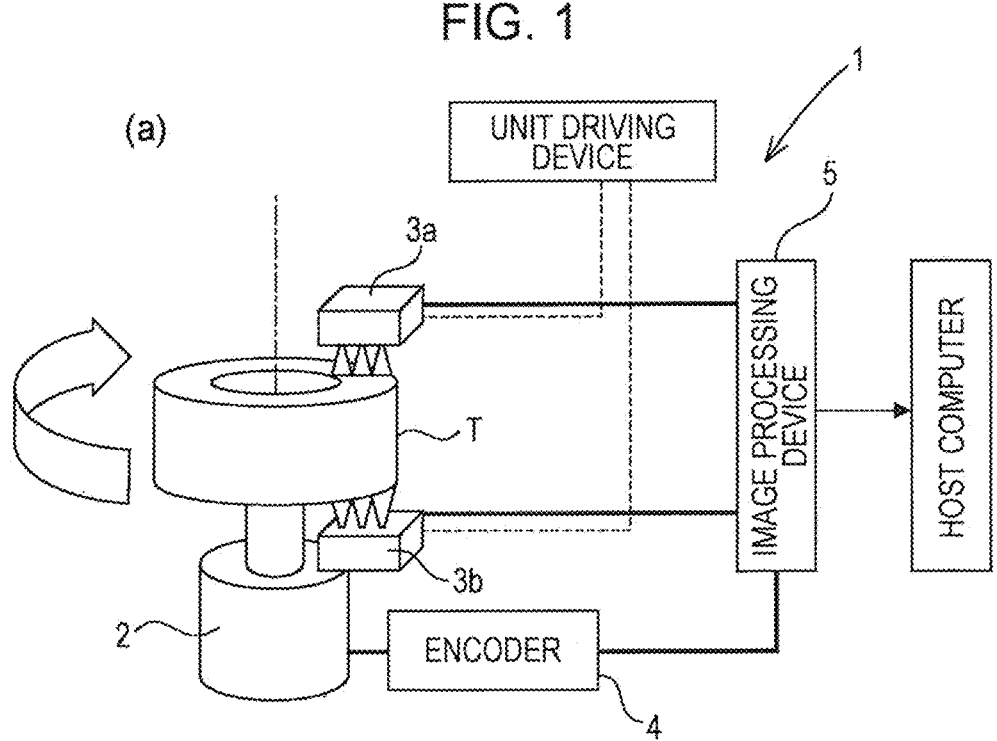
(b)
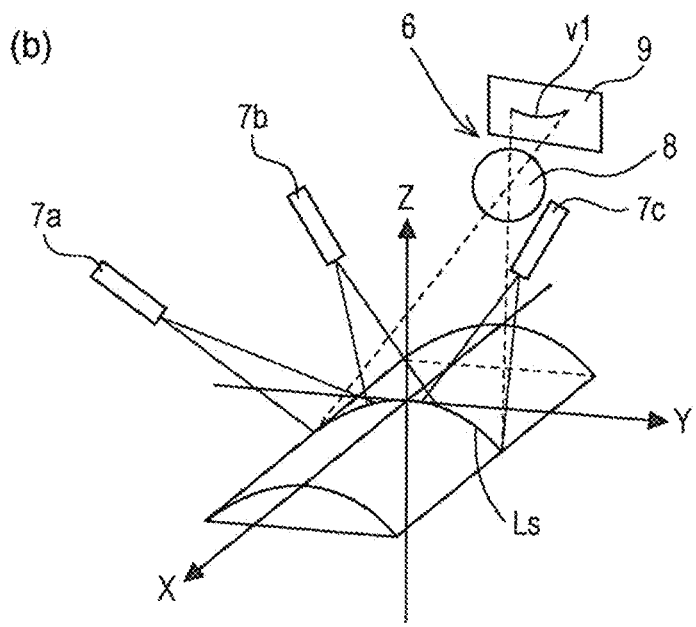

FIG. 8
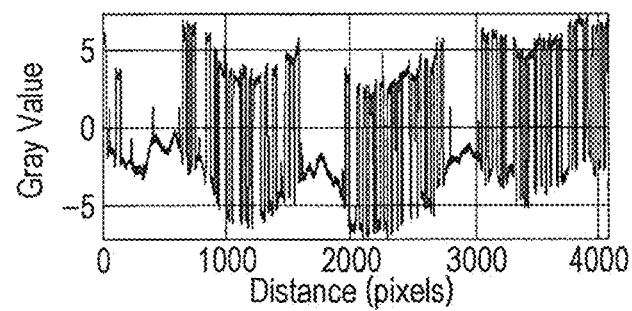
(b)
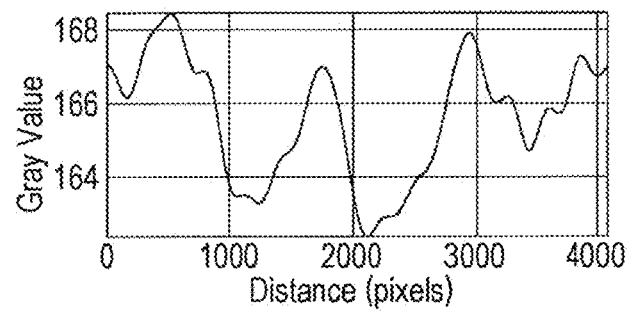
(e)
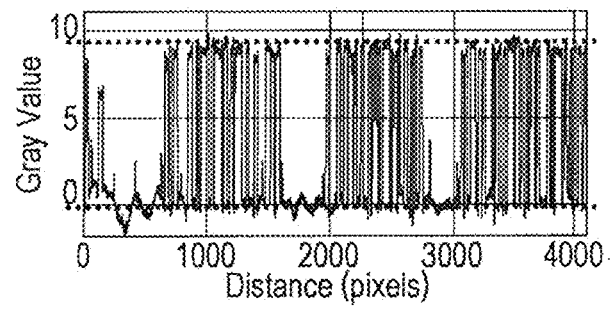
(f)

FIG. 9
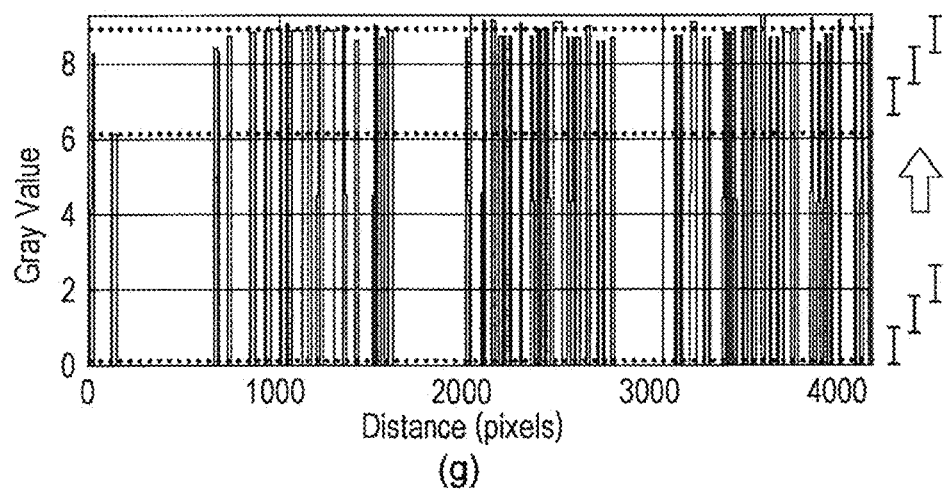
(g)
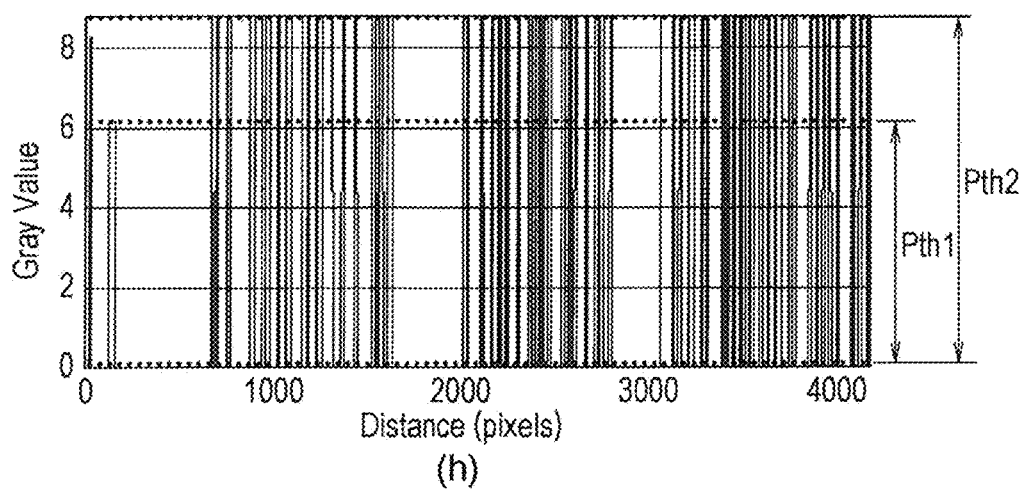
(h)

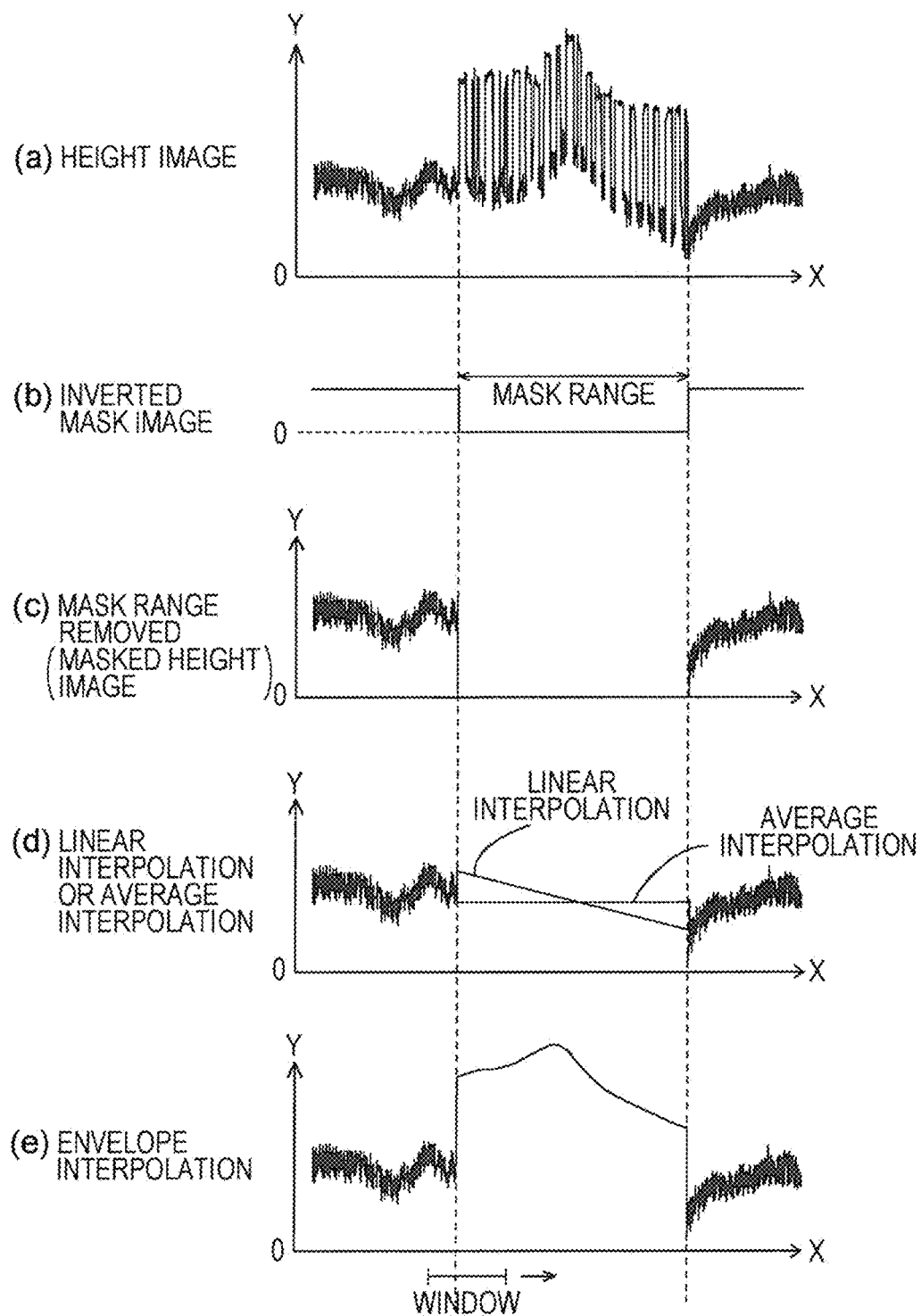

TIRE SHAPE INSPECTION METHOD AND TIRE SHAPE INSPECTION APPARATUS

TECHNICAL FIELD

The present invention relates to a tire inspection technique, and particularly relates to a tire shape inspection method and apparatus for inspecting a sidewall surface for shape defects by using an image processing technique, the sidewall surface having uneven (embossed) marks therein.

BACKGROUND ART

A tire has a structure formed by stacked layers of various materials, such as rubber, chemical fibers, and steel cords. If this layered structure has a non-uniform portion and the tire is filled with air, a raised portion called "bulge", or a recessed portion called "dent" or "depression", is formed in an area where resistance to pressure is relatively weak. In inspection, a tire with a shape defect, such as a bulge or dent, needs to be excluded from shipment due to safety concerns or problems with appearance.

Therefore, in the final stage of tire production (i.e., in an inspection step after tire vulcanization), tire surfaces, particularly sidewall surfaces, are inspected for defective unevenness or shape defects. The sidewall surfaces of a tire have indication marks (normal uneven marks) that indicate the model and size of the product, the logo of the manufacturer, etc. Therefore, in the process of inspecting the sidewall surfaces for shape defects, it is necessary that such indication marks be not erroneously detected as shape defects.

Conventionally, inspections for such defective unevenness or shape defects would be manually performed, both visually and by touching. In recent years, efforts have been underway to develop automated techniques, such as laser distance sensors, three-dimensional shape measuring apparatuses, and camera-based image inspections, and inspection techniques which are not affected by the presence of normal uneven marks.

For example, Patent Literature (PTL) 1 discloses a tire shape detecting apparatus that detects a surface shape of a tire by picking up an image of line light projected onto the surface of the tire rotating relatively, and performing shape detection by a light section method on the basis of the picked-up image. The tire shape detecting apparatus includes line light irradiation means for continuously projecting a plurality line light beams from directions different from a detection height direction in one light section line such that the one light section line is formed on the surface of the tire; and image pickup means for picking up images in a direction in which chief rays of the plurality of line light beams projected onto the surface of the tire are specularly reflected from the surface of the tire.

In particular, this tire shape detecting apparatus is configured to continuously project a plurality line light beams onto the tire surface, pick up images of the plurality of projected line light beams, and detect a tire surface shape.

PTL 2 discloses a method for inspecting three-dimensional shapes of one or more uneven (embossed) marks in a tire surface. The method includes a step of measuring heights of unevenness for each of area elements, including these marks, in a predetermined tire surface region to acquire unevenness distribution data; a step of identifying a tire surface portion corresponding to a mark model in the tire surface region, the mark model being prepared in advance as a mark template for each of the marks, from three-dimensional shape data of the mark model and the acquired unevenness distribution data; and a step of determining, for each of the marks, a degree of coincidence between the unevenness distribution data of the identified tire surface portion and the three-dimensional data of the mark model, and determining whether to accept the three-dimensional shape of the mark on the basis of the degree of coincidence.

In particular, this method for inspecting tire uneven marks performs inspection for detects by calculating a degree of coincidence between three-dimensional unevenness distribution data acquired by irradiating a tire surface with sheet light and three-dimensional shape data of a mark model generated from CAD data. In this technique, which determines whether to accept a normal uneven mark (e.g., text), a mark model prepared in advance as a template for the normal uneven mark is used as teaching data. The template is generated from tire CAD data or mold CAD data.

CITATION LIST

Patent Literature

PTL 1: Japanese Unexamined Patent Application Publication No. 2008-221896
PTL 2: Japanese Unexamined Patent Application Publication No. 2005-331274

SUMMARY OF INVENTION

Technical Problem

The tire shape detecting apparatus disclosed in PTL 1 is capable of detecting a tire surface shape by a light section method, and thus can detect an uneven shape of the tire surface. However, it is not possible to know whether the detected uneven shape of the tire surface is a normal mark in the tire surface or a defect. If there is a defect at the location of a normal mark, it is even more difficult to detect the defect.

If tire CAD data or mold CAD data is used to generate teaching data (reference data) as disclosed in PTL 2, it may be possible to obtain values not being affected by the presence of tire deformation or defects, and to avoid problems associated with the technique disclosed in PTL 1. However, because tires are rubber products, and because tires filled with air are inspected in the tire shape inspection which is a subject of this invention, the amount of tire deformation from CAD data is large. This means that an enormous amount of calculation and computation is required simply to match the corresponding coordinates, and it is difficult in practice to apply this technique.

Using data of actually measured tire heights as teaching data can be easily inferred from using CAD data which is a technique disclosed in PTL 2. This method facilitates acquisition of actual height data.

In this case, however, a tire height image used as teaching data needs to contain normal uneven marks only, and height image data needs to be completely free from defective unevenness (bulges and dents) to be detected, or from height variation in runout components which are large undulating deformation components in the tire circumferential direction. If height image data containing defective unevenness (detection objects) or runout components is used as teaching data, normal uneven marks, such as text, are planarized (removed) by subtraction processing during online inspection. However, defective unevenness or runout components present in the teaching data will be transferred to the height image to be inspected, and hence such height image data cannot be used for inspection. Also, it is not realistic to produce a perfectly smooth tire which is free from runout components, specifically for registration of teaching data.

In view of the problems described above, the present invention aims to provide a tire shape inspection method and a tire shape inspection apparatus with which it is possible to inspect a sidewall surface of a tire for defective unevenness, without being affected by the presence of normal uneven marks (e.g., text, logos, and patterns) in the sidewall surface.

Solution to Problem

To achieve the object described above, the present invention takes the following technical measures.

A tire shape inspection method according to the present invention is a method that inspects a sidewall surface of an inspection tire for shape defects by using an image of a sidewall surface of a sample tire having uneven marks in the sidewall surface thereof. The tire shape inspection method includes a teaching operation process and an inspection operation process. The teaching operation process includes a mask image generating step of detecting boundary lines which are contours of the uneven marks in a sample original image which is a two-dimensional image of the sidewall surface of the sample tire, and generating a mask image showing positions of the boundary lines; and a height offset image generating step of removing, from the sample original image, regions corresponding to the positions of the boundary lines shown in the mask image, and generating a height offset image by expressing heights of the remaining regions using one or a plurality of offset values. The inspection operation process includes a subtraction processing step of subtracting the height offset image from an inspection image which is a two-dimensional image of the sidewall surface of the inspection tire, and removing boundary regions shown by the mask image; and a shape defect detecting step of inspecting the sidewall surface of the inspection tire for shape defects on the basis of an unevenness-removed image obtained as a result of the subtraction processing step. The height offset image generating step generates, in the sample original image, an offset profile that approximates a base surface which is a sidewall surface having no uneven marks; extracts the uneven marks from the sample original image on the basis of the generated offset profile; and sets heights of the extracted uneven marks as the offset values.

The height offset image generating step may perform:

(I) extracting line data along a tire circumferential direction in the sample original image;

(II) extracting a base line of the sample tire on the basis of the line data;

(III) generating unevenness line data of the uneven marks by subtracting the base line data from the line data; and (IV) setting heights of the generated unevenness line data as offset values of the uneven marks.

The step (IV) described above may perform:

(IV-1) setting an evaluation window having a predetermined width in a height direction of an uneven mark portion;

(IV-2) determining an average value of unevenness line data included in the evaluation window while shifting the evaluation window in a height direction of the unevenness line data; and (IV-3) substituting the determined average value with a height of the uneven marks in the unevenness line data and using the height as the offset value.

In the mask image generating step, a differential image that emphasizes boundary line portions of the uneven marks may be obtained by applying a differential filter, and the mask image may be generated by binarizing the obtained differential image through application of a predetermined threshold value to the differential image.

Before application of the differential filter, an undetected point in the sample original image may be removed by interpolation; and the image from which the undetected point has been removed may be planarized by removing curvature components of the sidewall surface from the image from which the undetected point has been removed, on the basis of a profile shape of the sidewall surface.

The height offset image generating step may perform the following steps by using the plurality of offset values set for the sample original image, the mask image, and the uneven marks:

(I) extracting, from the mask image, line data corresponding to one line data along the tire circumferential direction in the sample original image;

(II) defining each of regions on the one line data in the sample original image as one label region, the regions being separated by boundary lines shown by the line data extracted from the mask image;

(III) defining a label region which is the longest of all the label regions, in the circumferential direction, as a height offset value calculation start region, or defining a region having the largest area of all the regions surrounded by the boundary lines shown by the mask image as a height offset value calculation start region;

(IV) determining a height difference between adjacent label regions sequentially from the calculation start region; and (V) setting an offset value which is the closest of the plurality of offset values to the determined height difference as a height offset value, for each pair of adjacent ones of all the label regions.

The height offset image generating step may generate the height offset image by repeating the steps (I) to (V) for every line data in the sample original image.

In the height offset image generating step, the mask image may be superimposed on the height offset image; and for each of the regions surrounded by the boundary lines shown by the mask image, a height offset value that most frequently occurs in the region may be set as a height offset value for the entire region.

The tire shape inspection method may further include an interpolating step of interpolating height coordinate values, in a mask range masked with the mask image used in the subtraction processing step within the image obtained by the subtraction processing step, by performing the processing of any of the following (I) to (III):

(I) selecting height coordinate values at two positions on both sides of the mask range, and assigning, to the mask range, height coordinate values obtained by linearly varying a value from one height coordinate value to the other height coordinate value;

(II) selecting height coordinate values at two positions on both sides of the mask range, and assigning, to the mask range, an average height coordinate value obtained by determining an average value of one height coordinate value and the other height coordinate value; and (III) providing a window that at least partially overlaps with the mask range and is shorter than the mask range, selecting a largest height coordinate value or a smallest height coordinate value of positions corresponding to the window in the inspection image while shifting the window from one end to the other end of the mask range, and assigning the selected height coordinate value to the mask range.

A tire shape inspection apparatus according to the present invention is an apparatus that inspects a sidewall surface of an inspection tire for shape defects by using an image of a sidewall surface of a sample tire having uneven marks in the sidewall surface thereof. The tire shape inspection apparatus includes image pickup means for picking up a two-dimensional image of the sidewall surface; mask image generating means for detecting boundary lines which are contours of the uneven marks in a sample original image which is a two-dimensional image of the sidewall surface of the sample tire, and generating a mask image showing positions of the boundary lines; height offset image generating means for removing, from the sample original image, regions corresponding to the positions of the boundary lines shown in the mask image, and generating a height offset image by expressing heights of the remaining regions using one or a plurality of offset values; subtraction processing means for subtracting the height offset image from an inspection image which is a two-dimensional image of the sidewall surface of the inspection tire, and removing boundary regions shown by the mask image; and shape defect detecting means for inspecting the sidewall surface of the inspection tire for shape defects on the basis of an unevenness-removed image obtained as a result of the subtraction processing step. The plurality of offset values are heights of the uneven marks obtained by generating, in the sample original image, an offset profile that approximates a base surface which is a sidewall surface having no uneven marks, and extracting the uneven marks from the sample original image on the basis of the generated offset profile.

The image pickup means may include line light irradiation means for irradiating the sidewall surface with one light section line, an image pickup camera configured to pick up an image of the line light with which the sidewall surface is irradiated, and a picked-up image memory configured to form a two-dimensional image of the sidewall surface by sequentially store one-line images picked up by the image pickup camera.

Advantageous Effects of Invention

With the tire shape inspection method and the tire shape inspection apparatus according to the present invention, it is possible to reliably inspect a sidewall surface of a tire for defective unevenness, without being affected by the presence of normal uneven marks (e.g., text, logos, and patterns) in the sidewall surface.

BRIEF DESCRIPTION OF DRAWINGS

FIG. 1(a) is a schematic view illustrating a configuration of a tire shape inspection apparatus according to an embodiment of the present invention, and FIG. 1(b) is a schematic view illustrating a three-dimensional arrangement of line light irradiation means and a camera in a sensor unit included in the tire shape inspection apparatus.

FIG. 8 illustrates height image data of uneven marks obtained by using a base line.

FIG. 9 is a schematic view illustrating a method for determining height offset values (stepped offset values) from height image data represented by non-step offset values.

FIG. 10 illustrates a method for interpolating height pixel values for an area corresponding to a mask range, in the tire shape inspection method according to the embodiment of the present invention.

DESCRIPTION OF EMBODIMENTS

Embodiments of the present invention will now be described with reference to the drawings.

A tire shape inspection apparatus 1 according to an embodiment of the present invention picks up an image of line light projected onto a surface of a rotating tire T with a camera, and measures a height of each part of the tire T by performing shape detection by a light section method on the basis of the picked-up image. Next, the tire shape inspection apparatus 1 substitutes the measured height of each part of the tire T with the corresponding brightness value and obtains a two-dimensional image (inspection image) of the surface of the tire T.

Next, the tire shape inspection apparatus 1 removes indication marks in a sidewall surface (base surface) on the basis of a "mask image" and a "height offset image" generated in advance by using the "inspection image" described above and a "sample original image" obtained by picking up an image of a sample tire (free from defects). Then, the tire shape inspection apparatus 1 inspects the tire surface for defects. The "sample original image", "mask image", and "height offset image" will be described in detail later on.

Although a tread surface and sidewall surfaces of the tire T may be measured in the shape inspection of the tire T, a sidewall surface is measured in the present embodiment.

Figure 2:
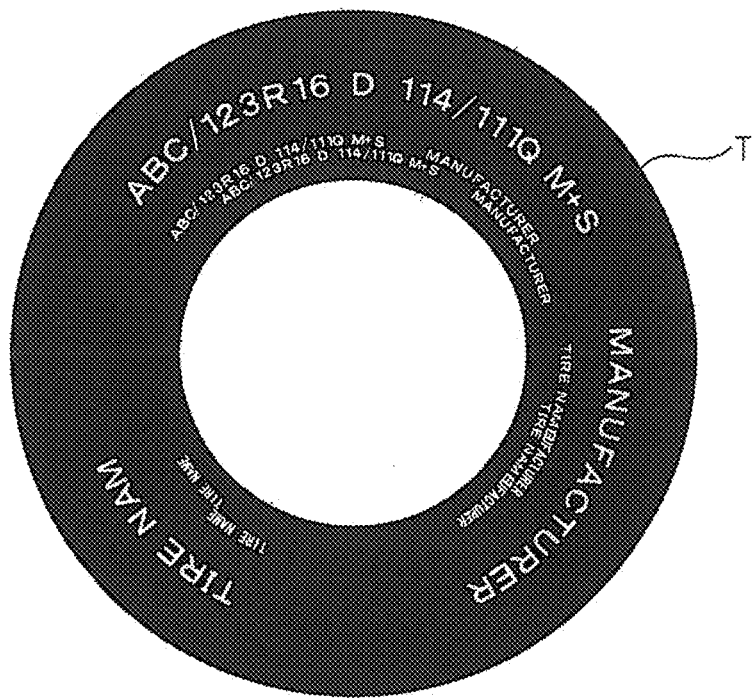
FIG. 2 is a schematic view illustrating a sidewall surface of a tire.

As illustrated in FIG. 2, a sidewall surface of the tire T is located between a tread surface that makes contact with a road surface and a bead fitted in a rim. Empty (white) portions in FIG. 2 are indication marks (normal figures, such as text, logos, and patterns) in the sidewall surface (base surface), and can be regarded as "normal uneven marks" (or embossed marks). The normal uneven marks are composed of raised and recessed portions having predetermined heights with respect to the base surface of the sidewall surface, the base surface having no normal uneven marks therein.

First, a general configuration of the tire shape inspection apparatus 1 according to an embodiment of the present invention will be described with reference to FIG. 1.

As illustrated in FIG. 1(a), the tire shape inspection apparatus 1 includes a tire rotator 2, sensor units (image pickup means) 3 (3a, 3b), an encoder 4, and an image processing device 5.

The tire rotator 2 is a rotating device including a motor that rotates the tire T, which is a shape inspection object, about the rotation axis thereof. For example, the tire rotator 2 rotates the tire T at a rotation speed of 60 rpm. During this rotation, the sensor units 3 (described below) detect a surface shape over the entire circumferential range of the sidewall surface.

In the present embodiment, two sensor units 3 (3a, 3b) are provided, which are used to measure the respective shapes of two sidewall surfaces of the tire T. The sensor units 3a and 3b are each a unit including line light irradiation means for irradiating a surface of the rotating tire T with line light (light section lines), and an image pickup camera 6 that picks up an image of line light reflected off the surface of the tire T.

FIG. 1(b) schematically illustrates an arrangement of devices included in each sensor unit 3.

In FIG. 1(b), a Y-axis represents a radial direction of the circumference of the tire T at a position for detecting the shape of the tire T, a Z-axis represents a detection height direction (i.e., a height direction of the surface to be detected) from the sidewall surface at a position for detecting the shape of the tire T, and an X-axis represents a direction orthogonal to both the Y-axis and the Z-axis. That is, in each sensor unit 3 used for shape detection of the sidewall surface of the tire T, the Z-axis is a coordinate axis parallel to the rotation axis of the tire T, and the Y-axis is a coordinate axis representing a direction of normal to the rotation axis of the tire T. Note that a correspondence between the tire T and the coordinate axes may vary depending on how the camera is supported.

The line light irradiation means is a device that includes a plurality of (three in FIG. 1(b)) line light sources 7a, 7b, and 7c. With the plurality of line light sources 7a, 7b, and 7c, the line light irradiation means continuously projects a plurality of line light beams, from directions different from the detection height direction (Z-axis direction) on one line Ls (light section line), such that one light section line is formed on the one line Ls on the surface of the tire T.

The image pickup camera 6 includes a camera lens 8 and an image pickup element 9. The image pickup camera 6 is configured to pick up an image v1 of the plurality of line light beams continuously projected onto the sidewall surface of the tire T (i.e., an image of the light section line on the one line Ls).

The tire rotator 2 is provided with the encoder 4. The encoder 4 is a sensor that detects a rotation angle of a rotation shaft of the tire rotator 2 (i.e., a rotation angle of the tire T), and outputs the detected rotation angle as a detection signal. The detection signal is used to control the image pickup timing of the image pickup camera 6 included in each of the sensor units 3a and 3b.

For example, a detection signal output from the encoder 4, every time the tire T rotating at a speed of 60 rpm rotates by a predetermined angle, is received, and then the image pickup camera 6 in each of the sensor units 3a and 3b is controlled such that a shutter is released in accordance with the reception timing of the detection signal. Thus, the image pickup operation is performed at a predetermined image pickup rate that matches the reception timing of the detection signal.

Signals (one-line images) from the sensor units 3a and 3b are input to the image processing device 5.

The image processing device 5 applies the principle of triangulation to each of the input one-line images to obtain height distribution information of a portion onto which the light section line is projected (i.e., one line portion on the sidewall surface). Next, the image processing device 5 substitutes the measured height of each part of the surface of the tire T with the corresponding brightness value, stores the brightness values in a frame memory (picked-up image memory) included in the image processing device 5, and obtains a two-dimensional image (inspection image) of the surface of the tire T.

The two-dimensional image (inspection image) is information in which measured surface heights (brightness values) at positions over the range of 360° in the circumferential direction of the sidewall surface are arranged in a two-dimensional coordinate system defined by the Y-axis representing the radial direction of the tire T and the X-axis (frame) representing the circumferential direction of the tire T.

The height distribution information corresponds to the graph of FIG. 7(b), and the inspection image and the sample original image correspond to the image illustrated in FIG. 7(a). Values (height pixel values) on the vertical axis in the height distribution information and brightness values of the inspection image have a one-to-one correspondence, and thus will be used synonymously in the following description.

On the basis of the obtained inspection image and the height distribution information corresponding to one line in this inspection image, the image processing device 5 of the present embodiment removes only the normal uneven marks from the inspection image, and applies an existing image processing technique to the resulting image to inspect the tire sidewall surface for defective unevenness present in abnormal uneven mark portions.

For example, the image processing device 5 is implemented by hardware formed by a personal computer.

Processing performed by the image processing device 5 of the tire shape inspection apparatus 1 according to the present embodiment will now be described.

Figure 3:
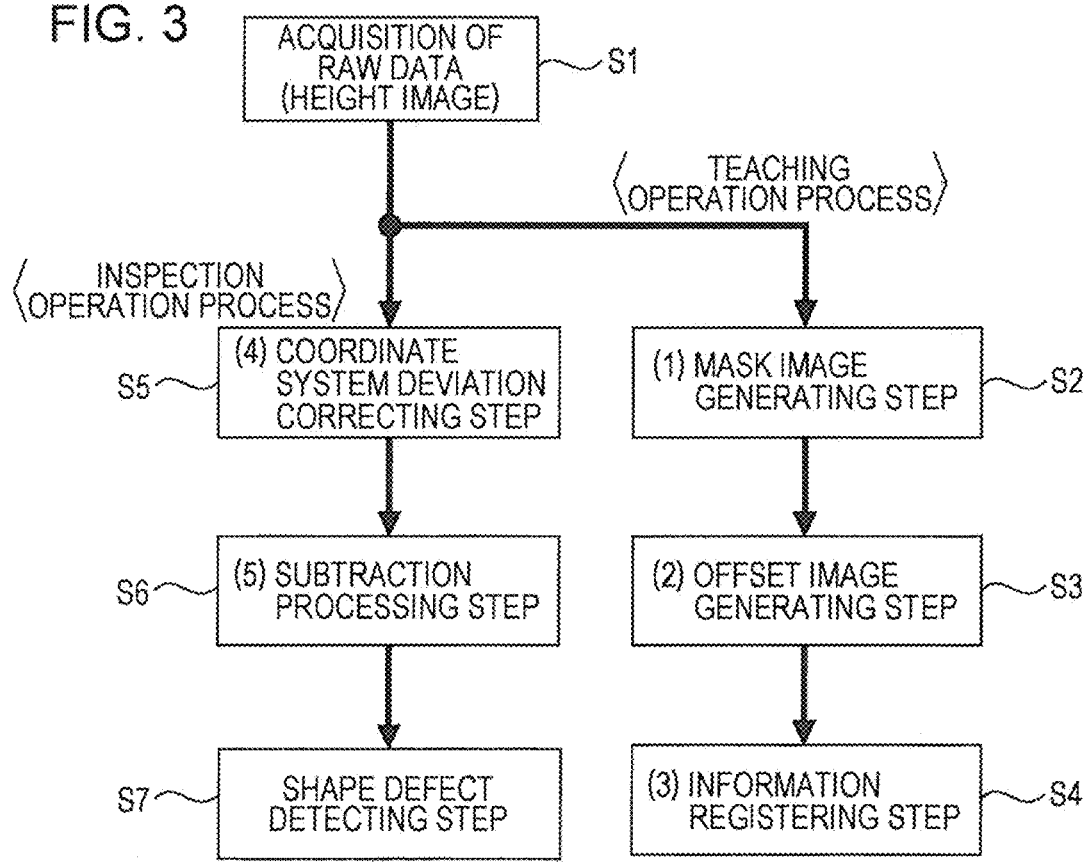
FIG. 3 is a flowchart illustrating processing of a tire shape inspection method according to an embodiment of the present invention.

FIG. 3 is a flowchart illustrating processing performed by the image processing device 5.

As can be seen from the drawing, the processing performed by the image processing device 5 includes an "inspection operation process" that performs an online inspection for defective unevenness in the sidewall surface of the tire, and a "teaching operation process" that precedes the inspection operation process.

The inspection operation process includes a "subtraction processing step (S6)" and a "shape defect detecting step (S7)". The "subtraction processing step (S6)" subtracts the height offset image from the inspection image which is a two-dimensional image of the sidewall surface of the inspection tire, and removes boundary regions shown by the mask image. The "shape defect detecting step (S7)" inspects the sidewall surface of the inspection tire for shape defects on the basis of a normal uneven mark-removed image obtained as a result of the subtraction processing step (S6). The steps S6 and S7 are performed by subtraction processing means and shape defect detecting means, respectively, included in the image processing device 5.

As illustrated in FIG. 3, the teaching operation process includes a "mask image generating step (S2)" and a "height offset image generating step (S3)". The "mask image generating step (S2)" detects boundary lines representing contours of the normal uneven marks in the sample original image which is a two-dimensional image of the sidewall surface of the sample tire, and generates the mask image showing positions of the boundary lines. The "height offset image generating step (S3)" removes regions corresponding to the positions of the boundary lines shown by the mask image from the sample original image, and generates the height offset image by classifying the heights of the remaining regions using offset values. The steps S2 and S3 are performed by mask image generating means and height offset image generating means, respectively, included in the image processing device 5.

Generally, there are multiple types of tires which are subjected to inspection. Therefore, as a registering operation before an online inspection, a setup operation is performed for each tire type (tire ID). The setup operation is an essential operation performed before the inspection. Specifically, the setup operation involves registering design information related to a tire shape, such as a tire diameter and a width of a contact surface (tread surface), which differs for each tire ID.

In the tire shape inspection of the present embodiment, the setup operation described above also precedes the inspection operation process.

The tire shape inspection method according to the present invention has distinctive features in the "subtraction processing step (S6)" of the inspection operation process and the "mask image generating step (S2)" and the "height offset image generating step (S3)" of the teaching operation process. The following will describe the details of the present tire shape inspection method while specifically referring to these steps.

Figure 4:
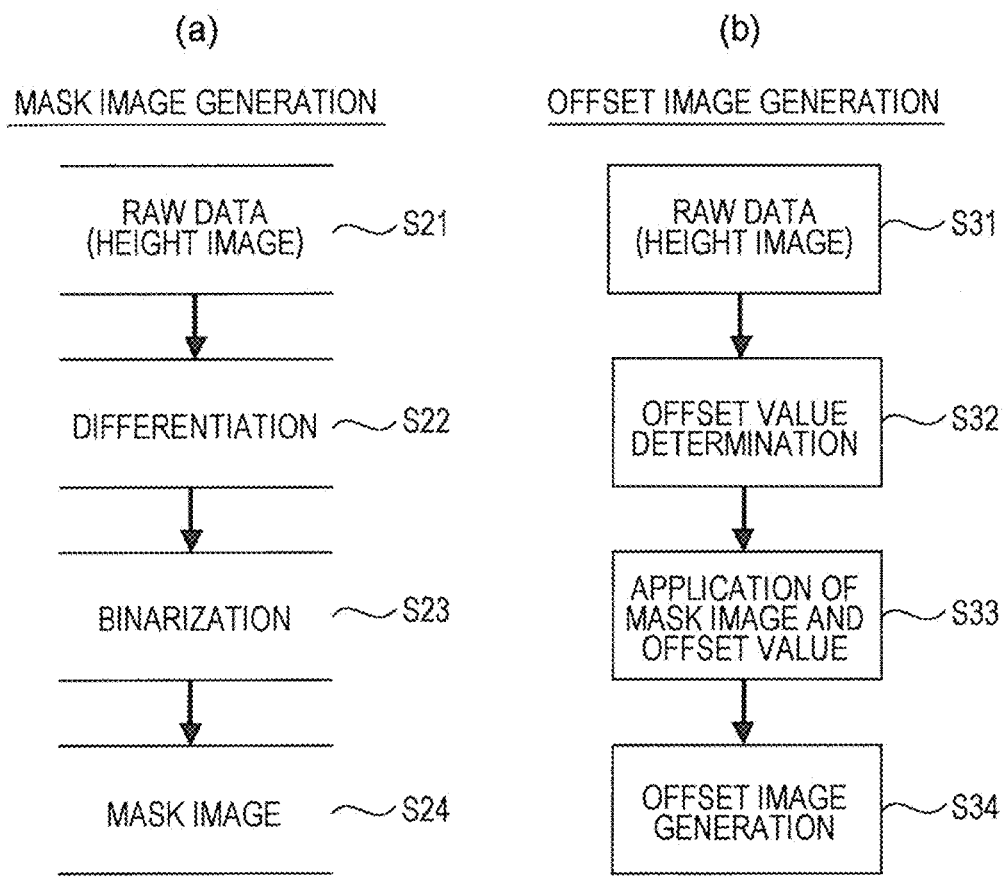
FIG. 4(a) is a flowchart illustrating a process of mask image generation in the tire shape inspection method according to the embodiment of the present invention.
FIG. 4(b) is a flowchart illustrating a process of offset image generation in the tire shape inspection method according to the embodiment of the present invention.

First, the teaching operation process will be described in detail with reference to FIG. 4.

First, a height image (raw data) of the sidewall surface of the sample tire, which is an ideal tire free from defects, is obtained.

The obtained height image (raw data) contains "undetected points". An undetected point is a point at which a height coordinate cannot be obtained because sheet light does not return to the camera due to level differences in the normal uneven marks, and hence the intensity of received light is below a specified value. A height coordinate 0 (black point) is output for the undetected point. A linear interpolation value is calculated by using height coordinates of two pixels for which the height coordinates have been detected, the two pixels being located near the undetected point and arranged in the tire circumferential direction on both sides of the undetected point. The calculated linear interpolation value is embedded as a coordinate of the undetected point.

Another method for determining a coordinate of an undetected point may be to copy a height near the undetected point without change (zeroth-order approximation), or to define a plane by four points surrounding the undetected point (two points in the circumferential direction and two points in the radial direction) and perform planar interpolation. If height coordinates of undetected points are left undefined, caution needs to be taken, because unexpected large differential values may be obtained in the subsequent smoothing differential processing and this may negatively affect the final detection of positions (boundary lines) of the normal uneven marks.

Generally, there are lower-order curvature components in a tire radial direction. Hence, the height image after the linear interpolation described above contains lower-order curvature components in the tire radial direction and the tire circumferential direction. If the subsequent smoothing differential processing step is performed without removing the curvature components, the differential values become larger due to the presence of the curvature components. The differential values resulting from the curvature components are difficult to distinguish from the differential values of the boundary lines of the normal uneven marks, which are actual objects of detection. Therefore, it is important to perform planarization that removes the curvature components from the height image after the linear interpolation.

The lower-order curvature components which are assumed to reflect tire design CAD data or mold CAD data can be corrected by using a shape model from such CAD data. In general, however, it is difficult for a system to make an association with CAD data. In the present embodiment, ideal curvature components are obtained directly from the obtained height image.

First, an average cross-sectional profile shape in a curvature component direction is determined. Then, for example, the curvature components are mathematically modeled by least-squares fitting of the cross-sectional profile shape to a quadratic curve, and the mathematically-modeled curvature components are removed from the height image after the linear interpolation.

Thus, the height image after the linear interpolation is planarized with a high degree of accuracy, with uneven figures, such as circumferential figures having a height coordinate that varies throughout the circumference, remaining in place. The sample original image illustrated in FIG. 5(a) is thus obtained (S21).

Next, the mask image generating step (S2) illustrated in FIG. 3 will be described.

The mask image generating step (S2) is shown as a flowchart of mask image generation in FIG. 4(a).

An image of differential values is obtained (S22) by performing differential filtering (two-dimensional smoothing differential filtering) using, for example, a Sobel filter or a Laplacian filter on the planarized height image (hereinafter referred to as sample original image) obtained by the processing (S21) described above.

For each line of the image of differential values obtained as described above, an average value (Ave) and a variance (1σ) are determined. The average values (Ave) and the variances (1σ) obtained as above are used to determine a binarization threshold value that separates the boundary lines of the normal uneven marks from background noise-like differential values. On the basis of this binarization threshold value, the image of differential values is binarized. Thus, the binarized image showing the boundary lines of the normal uneven marks is obtained (S23).

It is preferable that pixel points isolated in the obtained binarized image be removed by an isolated point removing filter, and that the boundary line portions of the normal uneven marks in the image obtained by removing the isolated pixel points be dilated by a dilation filter.

The image obtained by the processing described above is a mask image where values of binary pixel points in the boundary line portions are 1, and values of binary pixel points in the area other than the boundary line portions are 0. The mask image, such as that illustrated in FIG. 5(c), is stored in an internal memory of the image processing device 5 (S24).

The height offset image generating step (S3) in FIG. 3 will now be described with reference to FIG. 4 and FIGS. 6 to 9. The height offset image generating step (S3) is shown as a flowchart of offset image generation in FIG. 4(b). As in the mask image generating step (S2) described above, this step involves using the sample original image that has been subjected to linear interpolation and planarization (S31).

In the sample original image after planarization schematically illustrated in FIG. 7(a), a portion indicated by a solid line is part of a scan line and indicates a normal uneven mark portion. The graph of FIG. 7(b) shows, for example, a height pixel profile (cross-sectional shape) of the single scan line schematically illustrated in FIG. 7(a). As can be seen, there is low-frequency height pixel variation (low-frequency components), which represents undulations of the sidewall surface, throughout the profile, and there are abrupt changes in height pixel value in the normal uneven mark portion. Note that the low-frequency height pixel variation is represented, for example, by a low frequency of about the 20th to 70th order (about the 20th to 70th order after discrete Fourier transform).

In the height pixel profile shown in the graph of FIG. 7(b), a portion corresponding to the solid line in the sample original image is indicated by arrows. The normal uneven marks (uneven mark surfaces) shown here have substantially the same heights, but because they are located on the low-frequency height pixel variation (runout components) described above, their heights vary in accordance with the low-frequency height pixel variation.

The height pixel profile shown as line data in FIG. 7(b) is a collection of pieces of point data, each of which represents a brightness value (gray value) corresponding to a position coordinate (distance) on the sidewall surface. The pieces of point data are connected by line segments into a graph. This means that both end points of each line segment correspond to point data representing actual brightness values, and that the line segment excluding both the end points does not represent actual brightness value data.

The pieces of point data forming the height pixel profile are divided into those representing the base surface of the sidewall surface of the sample tire and into those representing surfaces other than the base surface, such as uneven mark surfaces, to generate an offset profile. For this, in the height pixel profile of FIG. 7(b), for example, the amount of difference (the amount of change) in brightness value between adjacent pieces of point data is detected sequentially from a position coordinate 0. Then, a variation in the absolute value of the amount of change shown in the graph of FIG. 7(c) is obtained.

That is, the graph of FIG. 7(c) shows a large value at a position where the brightness value in FIG. 7(b) changes significantly in the positive or negative direction. The graph of FIG. 7(c) shows that each position having a large value corresponds to a boundary between the base surface and a surface other than the base surface.

In FIG. 7(c), a determination threshold value Pth is set for the amount of change in brightness value represented by the vertical axis. Specifically, a determination threshold value set for the amount of change in brightness value is gradually increased from 0 in steps of the brightness value corresponding to a height of +0.1 mm. On the basis of each of the determination threshold values set as described above, each point data in the height pixel profile is classified into either a point data group for the base surface or a point data group for surfaces other than the base surface. Then, a difference (distance) between each point data and the determination threshold value is accumulated, and a determination threshold value corresponding to the smallest accumulated distance (or the smallest square error) is set as the final determination threshold value Pth.

In FIG. 7(c), each point data is compared to the determination threshold value Pth. Then, a position at which the amount of change represented by point data is greater than the determination threshold value Pth is determined to be a position indicating a "boundary between the base surface and a surface other than the base surface". Referring to FIG. 7(c), the amount of change represented by point data is greater than the determination threshold value Pth at positions P1, P2, P3, P4, and P5. Therefore, in FIG. 7(b), positions corresponding to the positions P1, P2, P3, P4, and P5 are each determined to be a position indicating a boundary between the base surface and a surface other than the base surface. In accordance with such a determination, each point data forming the height pixel profile shown in FIG. 7(b) is classified as either one that represents the base surface or one that represents a surface other than the base surface, such as an uneven mark surface.

For example, in FIG. 7(b), a flag indicating that the data is one representing the base surface is given to point data which is in the range from the position coordinate (distance) 0 corresponding to the base surface and at which the brightness value is small, to a position immediately before the position corresponding to the position P1 at which the amount of change in brightness value exceeds the determination threshold value Pth for the first time in FIG. 7(c).

Next, in FIG. 7(b), a flag indicating that the data is one representing a surface other than the base surface is given to point data which is in the range from the position P1 in FIG. 7(c) to a position immediately before the position corresponding to the position P2 at which the amount of change in brightness value exceeds the determination threshold value Pth for the second time. Thus, the flag indicating the base surface and the flag indicating a surface other than the base surface are switched from one to the other at each position where the determination threshold value Pth is exceeded, and are alternately given to the point data in FIG. 7(b) sequentially from the point data at the position coordinate (distance) 0.

Through this processing, each point data forming the height pixel profile shown in FIG. 7(b) is classified as either one that represents the base surface or one that represents a surface other than the base surface, such as a text surface.

Then, only point data that represents the base surface is extracted from the height pixel profile shown in FIG. 7(b) to obtain height pixel data representing the base surface. The height pixel data obtained here is data where point data representing surfaces other than the base surface is absent. The absent portions are linearly interpolated to generate height pixel data that represents the entire base surface.

Besides the linear interpolation, there is a method that can be used to generate height pixel data representing the entire base surface. For example, in FIG. 7(b), the determination threshold value Pth is subtracted from the brightness value of each point data representing a surface other than the base surface, and the resulting height pixel data is adjusted to the height pixel data representing the base surface. That is, heights of surfaces other than the base surface are lowered by the determination threshold value Pth and brought closer to the height pixel data of the base surface. Thus, by lowering the heights of surfaces other than the base surface by a predetermined value, height pixel data representing the entire base surface can be generated as in FIG. 7(d).

The height pixel data in FIG. 7(d) obtained as described above is apparently continuous data, but is actually data obtained by connecting pieces of discrete point data. Therefore, it is preferable that data be expressed as a continuous curve like an actual base surface of a sidewall.

FIG. 7(e) is a graph obtained by smoothing the graph of FIG. 7(d) using, for example, a low-pass filter. For example, after fast Fourier transform (FFT) of the height pixel data, the low-pass filter removes high-frequency components. It is assumed that the graph of FIG. 7(e) substantially accurately represents a low-frequency height pixel variation (runout components) on the base surface of the sidewall as a base line.

Next, the base line obtained as shown in FIG. 7(e) is applied to the line data in FIG. 7(b) to determine the height of each normal uneven mark (uneven mark surface). This method will be described with reference to FIG. 8.

FIG. 8 illustrates a procedure of correcting the line data by subtracting the runout components of the base surface shown in FIG. 7(e) from the line data shown in FIG. 7(b). By subtracting the runout components of the base surface from the line data as shown in FIG. 8, planarized height image data (unevenness line data) shown in FIG. 8(f) can be obtained, which is free from runout components (large undulations) and which substantially represents the heights of only the uneven marks. This planarized height image data is composed of planar portions having heights of around 0, and uneven mark surfaces having a plurality of different heights.

When mask processing is performed on the planarized height image data in FIG. 8(f) by using the mask image previously generated, the heights (pixel values) of boundary portions where abrupt changes take place become 0. Then, the planar portions are identified as a single label figure classified as a height 0 (clustering). Therefore, all the planar portions around the height 0 have a single value, the height 0 (black). Additionally, for each label region of the mask image, an average value (average height) of all pixel values contained in the label region is determined and set as a pixel value (height) of the label region. In the present embodiment, a plurality of different pixel values (heights), each obtained by averaging for each label region, will be referred to as non-step offset values.

FIG. 9(g) shows height image data expressed in a plurality of different values as non-step offset values. In FIG. 9(g), the heights of the uneven marks are expressed in the vicinity of two upper dotted lines. That is, in FIG. 9(g), two types of heights of the uneven marks are expressed in the vicinity of the two upper dotted lines. A method for detecting the two types of heights of the uneven marks from the height image data in FIG. 9(g) will now be described.

As shown on the right side of FIG. 9(g), an evaluation window having a predetermined width in the height (brightness value) direction is set. Then, the number of pieces of point data (all pieces of point data having height values within the evaluation window) is evaluated while the evaluation window is being shifted from the height 0 in the height direction.

First, in the vicinity of the lower of the two upper dotted lines shown in FIG. 9(g), the number of pieces of point data contained in the evaluation window begins to increase. Therefore, at around the height where the number of pieces of point data begins to increase, the position of the evaluation window containing a largest number of pieces of point data is detected. Then, at the detected position of the evaluation window, a brightness value having the smallest error with respect to each point data contained in the evaluation window is substituted for the point data contained in the evaluation window.

When the evaluation window is further shifted in the height direction, the number of pieces of point data contained in the evaluation window begins to increase in the vicinity of the upper of the two upper dotted lines. Again, the position of the evaluation window containing a largest number of pieces of point data is detected. Then, at the detected position of the evaluation window, a brightness value having the smallest error with respect to each point data contained in the evaluation window is substituted for the point data contained in the evaluation window.

The height image data expressed in the non-step offset values as in FIG. 9(g) is averaged, as indicated by two upper dotted lines in FIG. 9(h), at two types of heights (brightness values Pth1 and Pth2), that is, at stepped offset values. These two heights (brightness values) are used as two types of offset values for the uneven marks in the line data.

Figure 7:
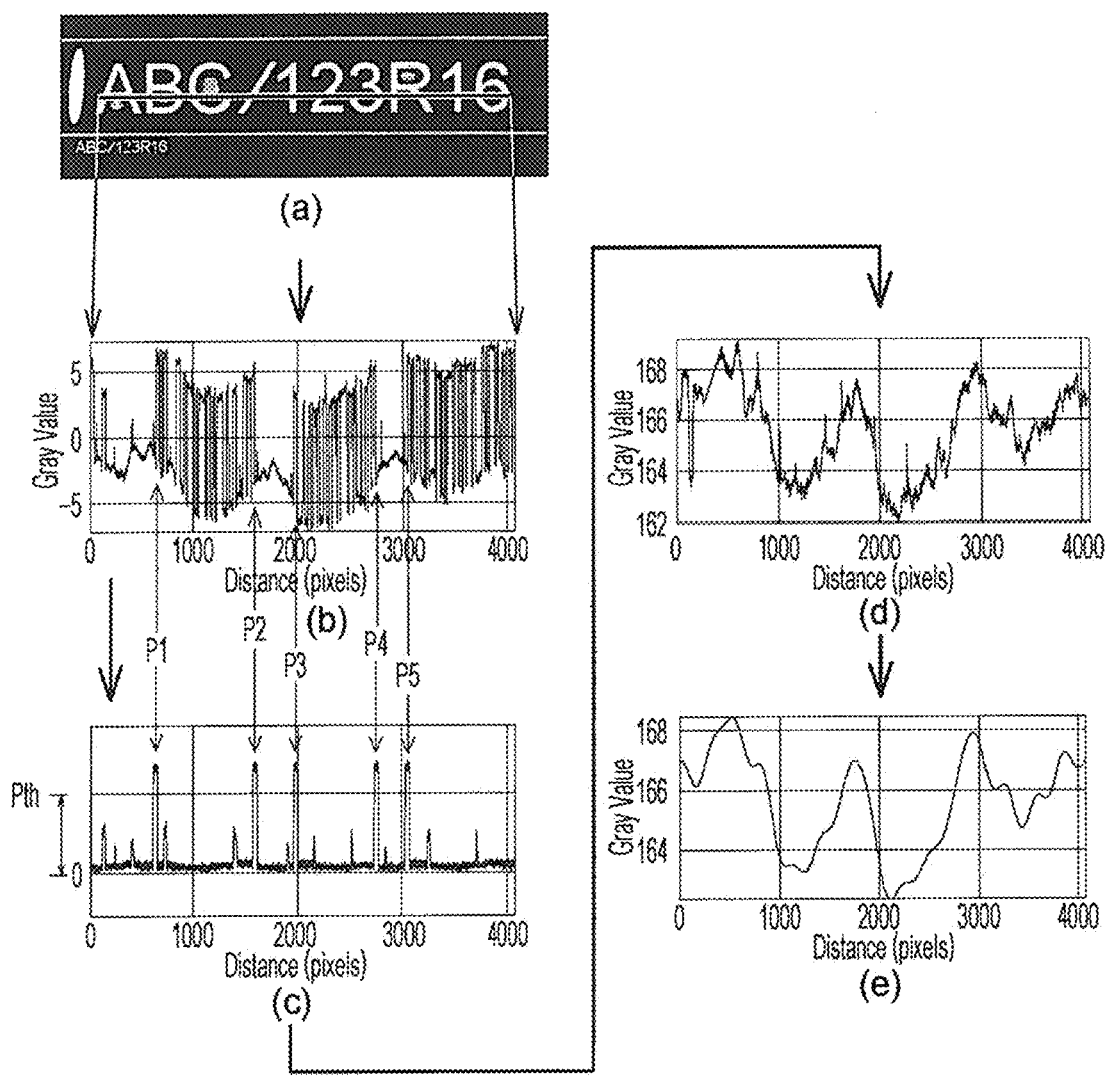
FIG. 7 is a schematic view illustrating a method for determining a base line in the tire shape inspection method according to the embodiment of the present invention.

A series of processing described with reference to FIGS. 7 to 9 is automatically performed, for example, by a computer program. Therefore, the offset values for the uneven marks can be automatically obtained without any manual intervention.

By using the above-described offset values for the uneven marks, a height offset image showing heights of the normal uneven marks is generated. This process will now be described.

Figure 6:
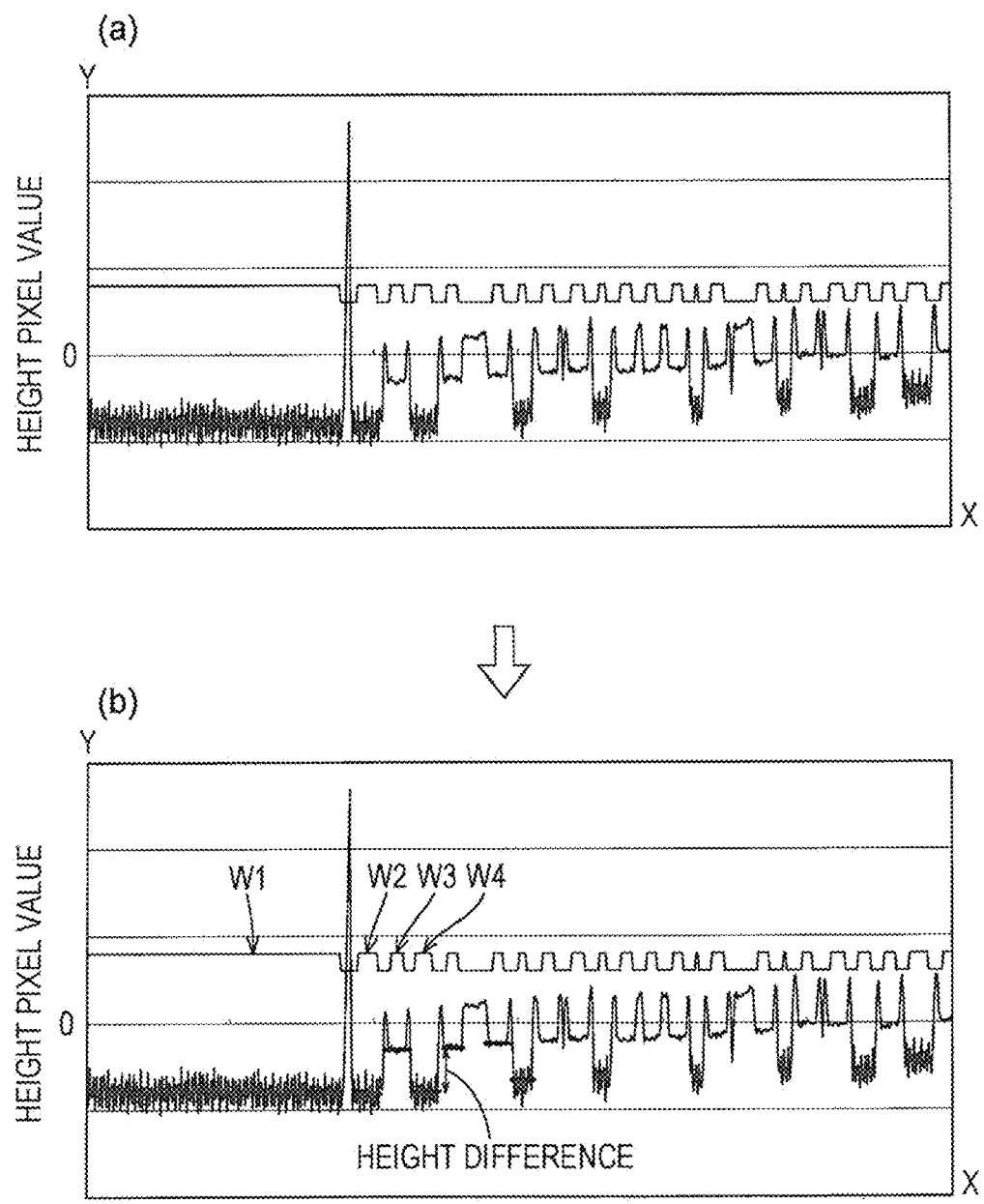
FIG. 6 illustrates a relationship between a height pixel profile and label regions in the tire shape inspection method according to the embodiment of the present invention.

FIG. 6 illustrates a relationship between a height pixel profile and label regions in the tire shape inspection method according to the present embodiment.

FIG. 6(a) is a graph showing an enlarged view of several hundreds of points along the X-coordinates in the tire circumferential direction, in one line of a height profile in the sidewall circumferential direction in the sample original image. A rectangular waveform in the graph is part of an inverted mask image generated by inverting the mask image previously determined. The rectangular waveform is an image at the same location as the height profile. As shown, the rectangular waveform is superimposed on the height profile.

The inverted mask image is a rectangular waveform that oscillates between the height pixel values 0 and 1, as in the non-inverted mask image. To make the graph easier to read, the inverted mask image is shifted in the positive direction of height pixel values.

In the inverted mask image, the values of binary pixel points in boundary line portions are 0, and the values of binary pixel points in portions other than the boundary lines are 1. In FIG. 6, regions corresponding to the height pixel value 0 in the inverted mask image indicate boundary line portions of the normal uneven marks. In the inverted mask image, regions corresponding to the height pixel value 1 and each separated by the boundary line portions are assigned respective label numbers. These regions are set as label regions.

A height offset of an average height in the longest label region W1 of these label regions (e.g., in FIG. 6(b), the label region in the leftmost part of the graph) is set to 0, and this label region is registered as a start region for height offset calculation. Then, in the longest label region described above, an average height in a portion near and including an end point in contact with a boundary line of a normal uneven mark, is determined from the height profile. Next, an average height in a label region W2 adjacent to the longest label region, with the boundary line therebetween, is determined. Then, a difference (height difference) between these two heights is calculated.

The resulting height difference is compared with the offset values of the uneven marks previously obtained. An offset value having the smallest difference from (or substantially the same as) the height difference described above is assigned as a height offset for the label region W2 adjacent to the longest label region W1, and is recorded in an offset image memory region.

Then, in a similar manner as above, a height difference between two adjacent regions W3, W4, and the like is sequentially calculated, and an offset value having the smallest difference from the resulting height difference is assigned as a height offset value (S33). After height offset values are assigned to one line throughout the circumference of the tire, similar assignment is performed on another line throughout the circumference. In this manner, height offset values are assigned to lines in the entire range of the sample original image. The height offset image shown in FIG. 5(b) is thus obtained (S34).

If the height image obtained during teaching is completely free from low-frequency runout components and the normal uneven marks have the same values as those of the tire design CAD data, the obtained sample original image (height image) may be registered as an offset image without using the "offset values of uneven marks" described above, or the determined height differences may be set as height differences between adjacent regions (relative offset values) without using the "offset values of uneven marks" described above.

However, tires which are rubber products filled with air are never free from runout components, and it is not practical to use the obtained sample original image as an offset image. If determined height differences are registered as continuous offset values, errors resulting from runout components accumulate during calculation for one circumference of the tire.

As a result, a height offset value at the end point of one line is not continuous with a height offset value at the start point of the line.

By using offset values of the uneven marks while reflecting the shape of the tire filled with air, the present technique estimates the heights of the normal uneven marks in the sidewall surface with a given offset. With this technique, it is possible to obtain an offset image for practical teaching.

In an information registering step (S4) in FIG. 3, the mask image and the offset image are registered in the image processing device 5. The teaching operation process ends here. Thus, after the teaching process, the tire sample image can be checked and corrected through a computer GUI, and hence the teaching operation can be completed in a short time.

After the teaching process described above, the inspection operation process (online inspection) is performed, which involves inspecting the sidewall surface of the tire (inspection object) for defective unevenness (bulges and dents).

Figure 5:
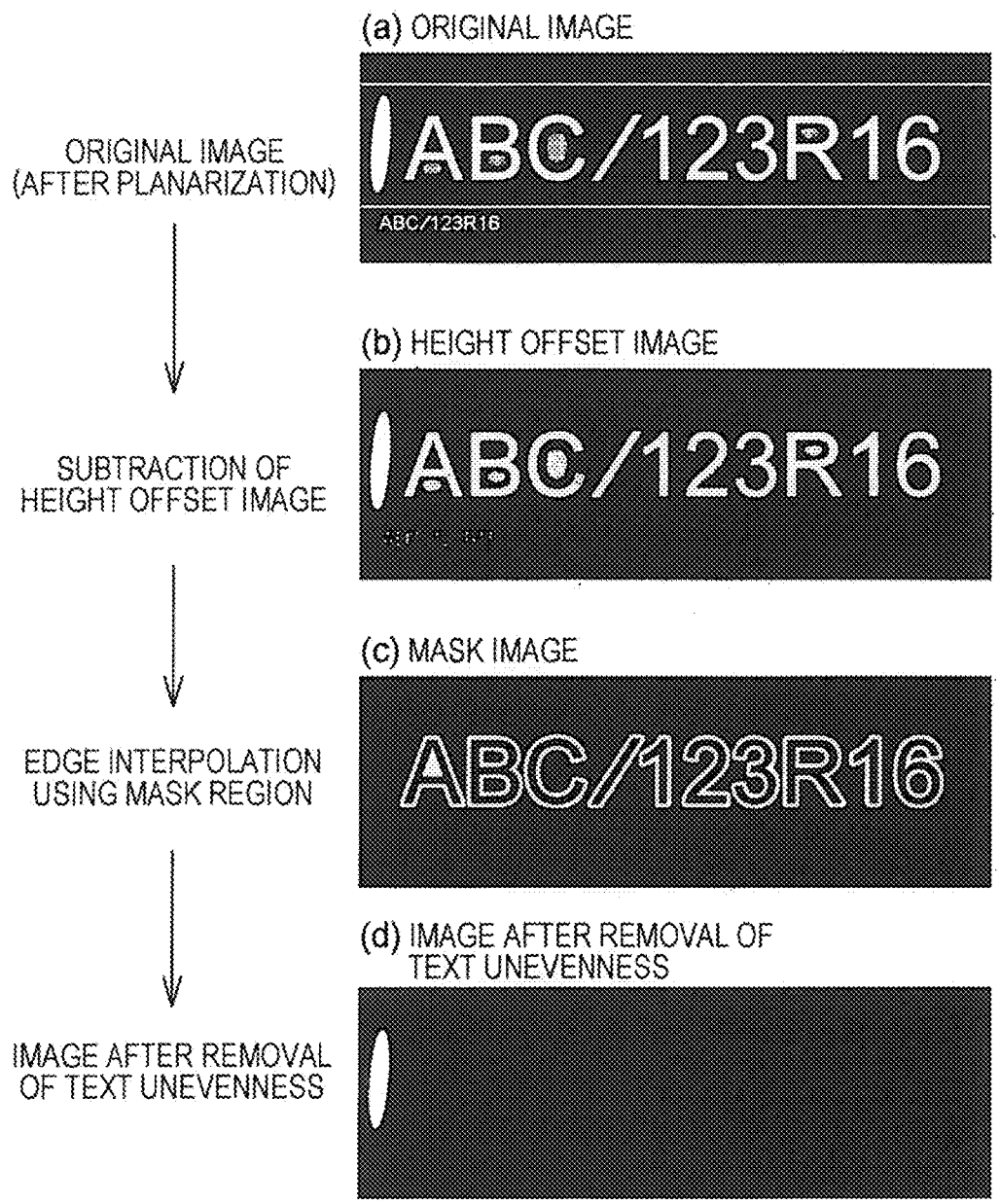
FIG. 5 is a schematic view illustrating a process of image processing in the tire shape inspection method according to the embodiment of the present invention.

The inspection operation process will now be described with reference to FIGS. 3 and 5.

In the inspection operation process, first, an original image (inspection image) of the sidewall surface of the tire under inspection, shown in FIG. 5(a), is obtained.

Next, in a coordinate system deviation correcting step (S5) in FIG. 3, a coordinate system deviation (which is mainly a phase difference in the circumferential direction or a rotation angle) of the inspection image is corrected. For position adjustment, image matching is performed for matching with the normal uneven marks (e.g., logos) in the sidewall surface, and a phase difference is corrected.

Next, in the subtraction processing step (S6) in FIG. 3, the height offset image registered during teaching is subtracted from the inspection image. Thus, a height image of the sidewall surface from which the heights of the normal uneven marks have been subtracted is obtained.

In this resulting height image, since data of boundary line portions (mask range) shown by the mask image does not necessarily indicate proper values, the boundary line portions are interpolated on the basis of the mask image. The interpolation processing will now be described.

For example, if the mask range on one line in the circumferential direction corresponds to several successive X-coordinate points, an average height coordinate of the ends of two respective normal uneven marks adjacent on both sides of the mask range in the mask image is determined. Linear interpolation is done by using the average height coordinate as a height coordinate for the mask range.

For example, if the mask range in the circumferential direction corresponds to several tens of successive X-coordinate points or more, a maximum or minimum height pixel value in a partial range smaller than or equal to the length of the mask range is selected within the mask range in the mask image. Then, the selected height coordinate value is used as a height coordinate for the mask range to interpolate all height coordinates within the mask range.

The image after removal of text unevenness illustrated in FIG. 5(d) is obtained by the processing described above.

The shape defect detecting step (S7) in FIG. 3 is performed using the image obtained after removal of text unevenness. In the image obtained after removal of text unevenness illustrated in FIG. 5(d), only height variation in the normal uneven marks is removed, and the height of a raised defect portion indicated by a white oval shape on the left side of the image is left unchanged from the original image (inspection image) illustrated in FIG. 5(a). The shape defect detecting step (S7) detects such a raised or recessed defect portion remaining in the image after removal of the text unevenness.

An existing image processing technique can be used in the shape defect detecting step (S7). Defect extraction based on binarization or pattern matching may be used.

By using the tire shape inspection method of the present invention described above, it is possible to reliably detect defective unevenness (raised defects or bulges, recessed defects or dents) having height variation similar to that of the normal uneven marks (e.g., text, logos, and patterns) in the sidewall surface of the tire without being affected by the presence of the normal uneven marks. In particular, a tire shape inspection can be performed without being affected by deformation specific to rubber products or by deformation caused by pumping air into the tire.

The embodiments disclosed herein should be considered illustrative, not restrictive, in all respects. The scope of the present invention is defined not by the above description but by the appended claims, and is intended to include meanings equivalent to the claims and all changes made within the scope.

For example, the mask image generating step (S2) and the height offset image generating step (S3) may be performed either automatically or manually by an operator with reference to the image. Each of the steps may be performed multiple times.

Specifically, in the image processing device 5, the inspection image, the mask image, the height offset image, and the image obtained after removal of the normal uneven marks may be displayed side by side or switched from one to another, so that the operator can check each image to see whether boundary lines originally intended to be connected are broken, or whether wrong portions are erroneously identified as boundary lines.

If any defects are found in the mask image in the checking operation, boundary lines may be added or deleted through the GUI, and the mask image may be recalculated after the correction. Next, the set height offset image is checked to see whether a single type of offset value set for each label is abnormal. If any defects are found, a region to be corrected may be specified to change the height offset value (increment or decrement the height offset value by 1), and the height offset image may be recalculated after the correction.

The image obtained after removal of the normal uneven marks shows a planarized state reached when an online inspection is actually performed on the basis of the teaching information currently set. The height image obtained after processing is checked and if there are any defects, it is preferable that the process be returned to checking and correcting the mask image or the height offset image, and that the image be corrected and recalculated.

The mask image generated in the present embodiment may include a mask range (mask region) larger than defective unevenness (bulges and dents) to be detected. If there is defective unevenness in such a large mask range, defective unevenness (bulges and dents) to be detected may be overlooked because of the masking. Therefore, it is preferable to carry out processing that interpolates height coordinate values. It is more preferable that the interpolation processing for the mask range be changed depending on the size (length) of the mask range.

With reference to FIG. 10, the interpolation processing (interpolating step) that follows the subtraction processing step (S6) in FIG. 3 will be described in detail. In FIG. 10, the X-axis represents the tire rotation direction (circumferential direction), and the Y-axis represents the amount of height variation of the tire surface.

As described above, in the subtraction processing step (S6), first, the height offset image registered during teaching is subtracted from the inspection image to obtain a height image of the sidewall surface of the tire. FIG. 10(a) shows a part of one line in the obtained height image.

In the height image shown in FIG. 10(a), there are many normal uneven marks having less pixels (i.e., short in length) in the X-axis direction which is the tire rotation direction, and portions which are boundary lines of these normal uneven marks and where the height coordinate value (height pixel value) abruptly changes are close to each other. Therefore, in the mask image obtained in the mask image generating step shown in FIG. 4(a), most of these normal uneven marks are within the mask range. The mask image obtained as above is inverted to obtain an inverted mask image.

FIG. 10(b) shows a portion of the obtained inverted mask image, the portion corresponding to the height image in FIG. 10(a). In the inverted mask image, values of binary pixel points in the mask range corresponding to the normal uneven marks in the height image are 0. By taking the logical AND of the inverted mask image and the height image, the area corresponding to the mask range in the height image in FIG. 10(a) is masked to make the height coordinate values 0. A masked height image shown in FIG. 10(c) is thus obtained.

In this masked height image, since the height coordinate values for the area corresponding to the mask range are all 0, the height coordinate values need to be interpolated for the masked area. There are three possible methods for interpolating the height coordinate values: linear interpolation, average interpolation, and envelope interpolation. If the area corresponding to the mask range in the masked height image is several pixels (e.g., less than 10 pixels) in length, the height coordinate values are interpolated by linear interpolation or average interpolation. If the area corresponding to the mask range in the masked height image is more than several pixels (e.g., 10 pixels or more) in length, the height coordinate values are interpolated by envelope interpolation.

Linear interpolation is, as shown in FIG. 10(d), a method in which interpolation is performed by connecting, with a straight line, the height coordinate values of the ends of two respective normal uneven marks adjacent on both sides of the area corresponding to the mask range in the mask image, and assigning the linearly varying value on the straight line as the height coordinate values for the area corresponding to the mask range.

Average interpolation is, as shown in FIG. 10(d), a method in which interpolation is performed by determining an average of the height coordinate values of the ends of two respective normal uneven marks adjacent on both sides of the area corresponding to the mask range in the mask image, and assigning the average of the height coordinate values (average height coordinate value) as the height coordinate values for the area corresponding to the mask range.

Envelope interpolation is, as shown in FIG. 10(e), a method in which interpolation is performed by setting, along the X-axis direction, a window which is a partial range in the area corresponding to the mask range, and assigning a largest height coordinate value in the window range as a height coordinate value for the area corresponding to the mask range.

A window setting method will be described. In the following description, the mask range shown in the inverted mask image in FIG. 10(b) is assumed to be, for example, 40 pixels in length in the X-axis direction. In the height image in FIG. 10(a), a point (leftmost point) having the smallest X-coordinate in the mask range is defined as a window center point. A range including the window center point and several pixels to the right and left of the window center point is defined as a window in the height image shown in FIG. 10(a). For example, if a window is set by including the window center point and 10 pixels each to the right and left of the window center point, the range of 21 pixels is set as the window, which has the leftmost point in the mask range as the window center point. It is generally preferable that the number of pixels in the window be about half or less than half the number of pixels in the mask range.

In the window defined as described, a largest height coordinate value is detected, and the detected value is assigned, as a height coordinate value of the position corresponding to the window center point, to the masked height image in FIG. 10(c).

Next, the window center point is shifted by one pixel in the X-axis direction, and a new window including the window center point after the shift is defined by the method described above. In the new window defined as above, a largest height coordinate value is detected, and the detected value is assigned to the masked height image as a height coordinate value of the position corresponding to the window center point.

This processing is repeated until the window center point reaches a position corresponding to a point (rightmost point) where the X-coordinate is largest in the mask range. Then when interpolation is performed by drawing an envelope with largest height coordinate values, the height coordinate values can be interpolated for the entire area corresponding to the mask range. FIG. 10(e) shows a height image obtained after the envelope interpolation. This substantially reproduces an approximate profile of the normal uneven marks shown by the height image in FIG. 10(a).

In the envelope interpolation described above, a largest height coordinate value in the window range is assigned as a height coordinate value of the position corresponding to the window center point. Alternatively, a smallest height coordinate value may be assigned as a height coordinate value in the mask range.

When a smallest height coordinate value is assigned, the resulting height image substantially reproduces an approximate profile of the base portion of the normal uneven marks shown by the height image in FIG. 10(a). That is, regardless of whether the largest or smallest height coordinate value is assigned, overall unevenness variation (represented by low-frequency components) in the mask range in the sidewall surface of the tire can be evaluated. An average of the largest and smallest height coordinate values in the window range may be assigned as a height coordinate value of the position corresponding to the window center point.

REFERENCE SIGNS LIST

1: tire shape inspection apparatus
2: tire rotator
3a, 3b: sensor unit
4: encoder
5: image processing device
6: image pickup camera
7: line light source
8: camera lens
9: image pickup element

The invention claimed is:
1. A tire shape inspection method that inspects a sidewall surface of an inspection tire for shape defects by using an image of a sidewall surface of a sample tire having uneven marks in the sidewall surface thereof, the tire shape inspection method comprising: at least one processor configured to implement:

a teaching operation process including
a mask image generating step of detecting boundary lines which are contours of the uneven marks in a sample original image which is a two-dimensional image of the sidewall surface of the sample tire, and generating a mask image showing positions of the boundary lines, and
a height offset image generating step of removing, from the sample original image, regions corresponding to the positions of the boundary lines shown in the mask image, and generating a height offset image by expressing heights of the remaining regions using one or a plurality of offset values; and
an inspection operation process including
a subtraction processing step of subtracting the height offset image from an inspection image which is a two-dimensional image of the sidewall surface of the inspection tire, and removing boundary regions shown by the mask image, and
a shape defect detecting step of inspecting the sidewall surface of the inspection tire for shape defects on the basis of an unevenness-removed image obtained as a result of the subtraction processing step,
wherein the height offset image generating step generates, in the sample original image, an offset profile that approximates a base surface which is a sidewall surface having no uneven marks, extracts the uneven marks from the sample original image on the basis of the generated offset profile, and sets heights of the extracted uneven marks as the offset values
wherein the height offset image generating step performs:
(I) extracting line data along a tire circumferential direction in the sample original image;
(II) extracting a base line of the sample tire on the basis of the line data;
(III) generating unevenness line data of the uneven marks by subtracting the base line data from the line data; and
(IV) setting heights of the generated unevenness line data as offset values of the uneven marks;
wherein the step (IV) performs:
(IV-1) setting an evaluation window having a predetermined width in a height direction of an uneven mark portion;
(IV-2) determining an average value of unevenness line data included in the evaluation window while shifting the evaluation window in a height direction of the unevenness line data; and
(IV-3) substituting the determined average value with a height of the uneven marks in the unevenness line data and using the height as the offset value.

2. The tire shape inspection method according to claim 1, wherein in the mask image generating step,
a differential image that emphasizes boundary line portions of the uneven marks is obtained by applying a differential filter; and
the mask image is generated by binarizing the obtained differential image through application of a predetermined threshold value to the differential image.

3. The tire shape inspection method according to claim 2, wherein before application of the differential filter,
an undetected point in the sample original image is removed by interpolation; and
the image from which the undetected point has been removed is planarized by removing curvature components of the sidewall surface from the image from which the undetected point has been removed, on the basis of a profile shape of the sidewall surface.

4. A tire shape inspection apparatus that inspects a sidewall surface of an inspection tire for shape defects by using an image of a sidewall surface of a sample tire having uneven marks in the sidewall surface thereof, the tire shape inspection apparatus comprising: at least one processor configured to provide:
image picker for picking up a two-dimensional image of the sidewall surface;
mask image generator for detecting boundary lines which are contours of the uneven marks in a sample original image which is a two-dimensional image of the sidewall surface of the sample tire, and generating a mask image showing positions of the boundary lines;
height offset image generator for removing, from the sample original image, regions corresponding to the positions of the boundary lines shown in the mask image, and generating a height offset image by expressing heights of the remaining regions using one or a plurality of offset values;
subtraction processor for subtracting the height offset image from an inspection image which is a two-dimensional image of the sidewall surface of the inspection tire, and removing boundary regions shown by the mask image; and
shape defect detector for inspecting the sidewall surface of the inspection tire for shape defects on the basis of an unevenness-removed image obtained as a result of the subtraction processing step,
wherein the plurality of offset values are heights of the uneven marks obtained by generating, in the sample original image, an offset profile that approximates a base surface which is a sidewall surface having no uneven marks, and extracting the uneven marks from the sample original image on the basis of the generated offset profile
wherein the height offset image generator performs to:
(I) extract line data along a tire circumferential direction in the sample original image;
(II) extract a base line of the sample tire on the basis of the line data;
(III) generate unevenness line data of the uneven marks by subtracting the base line data from the line data; and
(IV-1) set an evaluation window having a predetermined width in a height direction of an uneven mark portion;
(IV-2) determine an average value of unevenness line data included in the evaluation window while shifting the evaluation window in a height direction of the unevenness line data; and
(IV-3) substitute the determined average value with a height of the uneven marks in the unevenness line data and using the height as the offset value.

5. The tire shape inspection apparatus according to claim 4, wherein the image picker includes
line light irradiator for irradiating the sidewall surface with one light section line;
an image pickup camera configured to pick up an image of the line light with which the sidewall surface is irradiated; and
a picked-up image memory configured to form a two-dimensional image of the sidewall surface by sequentially store one-line images picked up by the image pickup camera.

* * * * *